United States Patent [19]

Schneider et al.

[11] Patent Number: 5,414,005
[45] Date of Patent: May 9, 1995

[54] METHODS AND ARTICLES OF MANUFACTURE FOR THE TREATMENT OF NICOTINE WITHDRAWAL AND AS AN AID IN SMOKING CESSATION

[75] Inventors: F. Howard Schneider, Yarmouthport; Indu A. Muni, North Reading, both of Mass.; B. Ram Murty, Lexington, Ky.; Mahendra K. Pandya, Massillon, Ohio; Rajinder P. S. Matharu, Lexington, Ky.

[73] Assignee: DynaGen, Inc., Cambridge, Mass.

[21] Appl. No.: 145,203

[22] Filed: Oct. 28, 1993

[51] Int. Cl.⁶ .................... A61K 9/20; A61K 31/465
[52] U.S. Cl. ........................ 514/343; 424/48; 424/435; 424/440; 424/441; 424/464; 424/465
[58] Field of Search ............... 514/343, 960; 424/440, 424/435, 441, 464, 465, 48

[56] References Cited

U.S. PATENT DOCUMENTS

| | | | |
|---|---|---|---|
| 3,789,840 | 2/1974 | Rosenblatt | 128/260 |
| 4,635,651 | 1/1987 | Jacobs | 131/271 |
| 4,971,079 | 11/1990 | Talopin et al. | 131/359 |
| 5,055,478 | 10/1991 | Cooper et al. | 514/343 |

FOREIGN PATENT DOCUMENTS

| | | |
|---|---|---|
| 4627 M | 1/1967 | France. |
| 2369845 | 6/1978 | France. |
| 1911112 | 9/1970 | Germany. |
| 1017032 | 1/1966 | United Kingdom. |
| 1056214 | 1/1967 | United Kingdom. |

OTHER PUBLICATIONS

Fed. Regist. 58(103):31236–41 1 Jun. 1993 per C.A. 119:34165y 1993 "Smoking deterrent drug products for over-the-counter use".

Davison et al. Psychological Report 31(2):443–456 Oct. 1972 as abstracted "Lobeline and reduction of smoking".

*Primary Examiner*—Shep K. Rose
*Attorney, Agent, or Firm*—Wolf, Greenfield & Sacks

[57] ABSTRACT

The present application features methods and articles of manufacture for alleviating acute symptoms of nicotine withdrawal and as an aid in smoking cessation. The invention features lobeline held in sublingual tablets for administration to the sublingual and nasal mucosa.

12 Claims, No Drawings

5,414,005

METHODS AND ARTICLES OF MANUFACTURE FOR THE TREATMENT OF NICOTINE WITHDRAWAL AND AS AN AID IN SMOKING CESSATION

FIELD OF THE INVENTION

The present invention features methods and articles of manufacture for the administration of lobeline to humans for the purpose of reducing symptoms of tobacco or nicotine withdrawal and as an aid in smoking cessation.

BACKGROUND OF THE INVENTION

Greater understanding of the adverse health effects of tobacco consumption and associated nicotine intake has led to a marked increase in research on the nature of nicotine addiction and its treatment. Addiction to nicotine, as described in past U.S. Surgeon General's reports on smoking, is widespread, with over 50 million smokers in the United States alone. Addiction to nicotine is a major barrier to an individual's ability to successfully and permanently stop smoking.

As with other addictions, addiction to nicotine encompasses two key components. One component is a physiological addiction to nicotine itself. The physiological addiction is mediated through adaptive changes in specific brain nicotine receptors that lead to typical withdrawal symptoms upon abstaining from nicotine. A second component is a complex behavioral component. The behavior component is linked to learned internal cues associated with various positive or negative emotional feelings tied to tobacco smoking or abstinence.

The physiological addiction to nicotine is significant. The American Psychiatric Association's Diagnostic and Statistical Manual of Mental Disorders (third edition, revised) lists the officially recognized diagnostic criteria for nicotine withdrawal as the presence of at least four of the following signs: (1) craving for nicotine; (2) irritability, frustration, anger; (3) anxiety; (4) difficulty concentrating; (5) restlessness; (6) decreased heart rate; and (7) increased appetite or weight gain.

Differing approaches to smoking cessation attempt to address the physiological addition and the behavior component. The approaches range from stopping "cold turkey," hypnosis, electroshock, acupuncture, behavioral counseling, to various forms of therapeutic support. Nicotine replacement therapies such as chewing gum and transdermal patches, in conjunction with behavioral counselling, are now commonly used to treat nicotine withdrawal and as an aid to smoking cessation. However, long-term success through the use of nicotine replacement is low. In general, 25% or less of the individuals attempting to stop nicotine use are abstaining 12 months after treatment.

There is a great need for treatment systems which promote permanent smoking cessation. There also is a need for products that provide temporary relief of tobacco/nicotine withdrawal symptoms for individuals who use tobacco products, when such use is temporarily interrupted.

Individuals who use tobacco, and do not intend to stop such use, must often refrain from such use for extended periods of time. Airline personnel and passengers, hospital workers and patients, individuals working in chemical plants or with flammable materials and the like may need to temporarily curtail the use of tobacco products. The occurrence of nicotine withdrawal is also frequently associated with reduction in task performance efficiency. Prevention of nicotine withdrawal may alleviate or prevent such reductions in task performance.

Individuals who have stopped tobacco use and are past acute withdrawal symptoms often have acute nicotine cravings. A reduction in nicotine craving is useful for such individuals encountering situations that increase their urge to use tobacco. Such relief may increase the individual's ability to maintain abstinence from tobacco use.

Lobeline is the principal alkaloid obtained from the dried leaves and tops of *Lobelia inflata,* an annual plant of the Lobeliaceae family. Lobeline is a substituted piperidine compound that produces several physiological effects, some of which are similar to those produced by nicotine. It is believed that the pharmacological actions of lobeline are produced by its ability to bind to nicotine receptors in the brain and elsewhere in the body. Lobeline's potency in causing peripheral pharmacological effects, such as increases in blood pressure and heart rate, is significantly less than that of nicotine.

Lobeline has been proposed as a substitute for nicotine, to reduce dependence on nicotine and reduce the use of tobacco products. Although use of lobeline as a smoking cessation aid has been studied since at least the 1930's, its efficacy has been a matter of dispute.

Typical over-the-counter (OTC) products providing lobeline comprise Nicoban TM, Bantron TM, CigArrest TM, NicFit TM and Smoker's Choice TM. All lobeline containing smoking cessation products sold in recent years have been non-prescription OTC products. The FDA reports that all OTC smoking cessation aids are ineffective and has taken the unusual step of declaring all such OTC products mislabeled in order to remove such products from the market. Most of the OTC products administered lobeline orally for absorption in the gastrointestinal tract. The directions with such products recommend a daily dose of up to 6 milligrams. Antacids are incorporated in some of the products to overcome gastrointestinal discomfort, a side-effect similar to that caused by nicotine. Higher oral doses may not be feasible because of the concomitant gastric upset.

Although there have been reports of using lobeline in oral formulations at doses in excess of 10 mg/day, nausea and even vomiting have been associated with such doses. A further problem with such oral dose regimens is that self-administration of as many as 18 tablets per day has been required. Patients may consider such a dosing regimen as intrusive, and such dosing regimen does not permit the physician to carefully control the administration of the drug or monitor patient compliance.

Lobeline is poorly absorbed from the gastrointestinal tract. Subjects desiring to substitute lobeline for nicotine are unable to take effective quantities of lobeline orally, due to adverse gastrointestinal effects. The oral products may not produce effective blood or tissue levels.

One product presently available, Smoker's Lozenges, contains lobeline in a candy lozenge. The lozenge is intended to dissolve slowly in the mouth to release lobeline. A second product, Smoker's Gum, contains lobeline in a gum base. The gum is intended to release lobeline slowly as the gum is chewed. The instructions with these products do not instruct users to retain the dissolved candy or gum fluids in the oral cavity. The normal reflex would urge users to swallow, severely limiting any buccal absorption of lobeline. Absorption of swallowed lobeline from the gastrointestinal tract may not avoid first pass metabolism by the liver.

These OTC products, as with other lobeline OTC products, have been subjected to FDA action questioning the efficacy of the formulation. It was believed that effective doses of lobeline could not be obtained without an invasive dosage form, such as injection.

The present invention is directed methods and articles of manufacture for delivering an effective amount of lobeline to the sublingual mucosa. The methods and articles of manufacture of the present invention provides relief from acute nicotine withdrawal, in a manner previously believed unattainable in a non-invasive dosage form. Such relief from acute nicotine withdrawal is directly applicable to individuals wanting to (1) temporarily abstain from smoking or otherwise using nicotine without suffering the full extent of nicotine withdrawal symptoms, or (2) cease using nicotine-containing products.

SUMMARY OF THE INVENTION

The present invention features methods and articles of manufacture for the treatment of nicotine withdrawal symptoms. One method of the present invention comprises administering to a subject an effective amount of lobeline or a lobeline analog to the sublingual mucosa prior to or during a period in which the subject is experiencing nicotine withdrawal symptoms. The lobeline is absorbed through the sublingual mucosa to alleviate the subject's desire for nicotine.

The term "nicotine" refers to the active ingredient of tobacco products. Nicotine has the formula represented below:

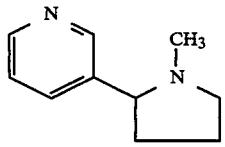

Lobeline refers to: 2-[6-(β-hydroxyphenethyl)-1-methyl-2-piperidyl] acetophenone. Lobeline is represented by the formula below.

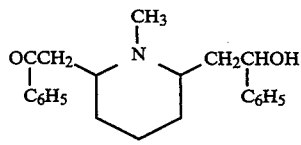

The term "lobeline" as used herein includes lobeline free base and its various salts. Functional groups may be added or deleted from the formula above, while retaining the physiological activity of lobeline. Such alterations and deviations are encompassed within the term "lobeline analogs."

The term "administering" means applying as a remedy, such as by the placement of a drug in a manner in which such drug would be received and be effective in carrying out its intended purpose.

An "effective amount" is an amount of a drug which, if administered to a subject will cause a desired therapeutic effect.

The term "sublingual" refers to the area of the oral cavity below the tongue. The term "nasal" refers to the air passages extending from the nose to the lungs. The term "mucosa" refers to a mucous membrane.

The term "subject" refers to an individual who is to be treated.

As used herein, long-term or sustained action refers to an action or duration of greater than 12 hours. As used herein, "short-term" means within a five minute period of time.

Preferably lobeline is administered as a soluble salt. Soluble salts of lobeline comprise hydrochloride, sulfate or palmoate salts. A preferred soluble salt comprises the hydrochloride or the sulfate salt which are more soluble than the palmoate. Most preferably, the soluble salt is the sulfate salt.

Preferably, lobeline is administered in an amount equivalent to 0.6 to 7.5 mg of lobeline free base. This amount of lobeline provides an effective level of lobeline through the sublingual mucosa to alleviate nicotine withdrawal symptoms.

One embodiment of the present method features lobeline administered as a sublingual tablet. As used herein, the term "tablet" refers to pharmaceutical dosage forms prepared by compressing or molding. Sublingual tablets are small and flat, for placement under the tongue and designed for rapid, almost instantaneous disintegration and release of drug to the sublingual mucosa. As used herein, the term "tablet" specifically excludes gums and lozenge dosage forms.

The term "disintegration" means to break apart; and, as used herein, specifically excludes breaking apart as a result of chewing, sucking and grinding in the oral cavity.

Preferably, the sublingual tablets of the present invention disintegrate, to release lobeline for rapid absorption by the mucosa, within five minutes and, more preferably, within a two minute period of time. Lobeline released rapidly to the sublingual mucosa is absorbed and transported to active sites in the brain, mimicking the rapidly increasing nicotine blood levels individuals experience when smoking. Thus, embodiments of the present method are ideally suited for treating acute nicotine withdrawal. Embodiments are also ideally suited to treat transient cravings for nicotine often experienced by smokers treated with long acting nicotine replacement therapy.

Sublingual administration of lobeline avoids first pass metabolism by the liver. Thus, lobeline absorbed by the mucosa is most effective in addressing withdrawal symptoms.

Preferably the tablet comprises a taste masking flavoring, such as peppermint, spearmint and the like to improve user acceptance.

One embodiment of the present invention features, as an article of manufacture, a dosage form for treating nicotine withdrawal symptoms comprising an effective amount of lobeline or lobeline analogs for application to the sublingual mucosa. The lobeline is absorbed through the mucosa to alleviate nicotine withdrawal symptoms.

The term "dosage form" refers to a pharmaceutical preparation for administering drug to a subject.

Preferably, the dosage form administers the equivalent of 0.6 to 7.5 mg of lobeline free base per dose. Preferably, the lobeline is held in the dosage form as a soluble salt.

A preferred dosage form is a sublingual tablet. Preferably, the sublingual tablet disintegrates and releases lobeline to the sublingual mucosa within a five minute period of time and most preferably within two minutes.

Embodiments of the present invention feature administering lobeline for acute nicotine replacement therapy. Embodiments of the present invention are ideally suited for co-therapy with long-acting, sustained release drug formulations. One embodiment of the present invention features a method of treating nicotine withdrawal symptoms comprising the steps of administering to a subject an effective amount of nicotine or lobeline by a sustained release drug formulation prior to or during a period in which the subject is experiencing nicotine withdrawal symptoms. The nicotine or lobeline released from the sustained release drug formulation provides a base level of nicotine or lobeline to substantially alleviate the subject's desire for nicotine. The method further comprises the step of administering to the subject an effective amount of lobeline to the sublingual mucosa prior to or during a period in which the subject is experiencing acute nicotine withdrawal symptoms. The lobeline absorbed through the sublingual mucosa alleviates the subject's short-term or immediate desire for nicotine in situations in which the withdrawal symptoms may be more intense.

The sustained release delivery system drug formulation may comprise a transdermal patch, or injectable of biodegradable polymers carrying lobeline for sustained release for subcutaneous, intramuscular or intradermal administration.

Other features and advantages of the present invention will be apparent from the following description which depict or describe preferred embodiments of the present invention and the principles thereof and what is now considered to be the best mode to apply these principles.

DETAILED DESCRIPTION OF THE INVENTION

The present invention is described in detail as methods and articles of manufacture for the treatment of nicotine withdrawal symptoms. One method of the present invention comprises the step of administering to a subject an effective amount of lobeline or lobeline analog to the sublingual mucosa prior to or during the period in which the subject is experiencing nicotine withdrawal symptoms. The lobeline or lobeline analog is absorbed through the sublingual mucosa to alleviate the subject's desire for nicotine.

The present invention features the administration of lobeline through rapid release dosage forms such as sublingual tablets.

Embodiments of the present invention are well suited for a wide variety of situations which may give rise to tobacco or nicotine withdrawal symptoms. For those active tobacco users who want to stop permanently, the present method and articles of manufacture allow for the immediate dosing of the subject, on an individual need basis. Coupled with appropriate behavior modification counselling, the present method and articles of manufacture can be an important part of a smoking cessation program.

For subjects who need to abstain from tobacco and nicotine, due to hospitalization or other medical necessities, embodiments of the present invention provide for a suitable nicotine replacement. Smokeless administration of nicotine by patches and the like is not suitable for many hospitalized patients due to its effects on heart rate and blood pressure. Lobeline has little effect on blood pressure and heart rate. Moreover, individuals who want to abstain from nicotine for a short time may resume their tobacco use upon release from the hospital without any concern regarding the lingering effects of administration with long-acting nicotine or nicotine substitutes.

In situations which require individuals to abstain from smoking due to restrictions encountered in every day situations, such individuals are able to alleviate nicotine withdrawal symptoms with a rapid acting nicotine substitute. For example, airline personnel and passengers are often unable to utilize tobacco products during flight. Embodiments of the present invention feature the administration of lobeline in a fast acting form with no lingering effects which would be expected in long-acting patches or other sustained delivery forms. Thus, individuals upon the completion of the period of time in which they are unable to utilize tobacco products, may resume their customary usage of tobacco products.

Embodiments of the present method and articles of manufacture have application in situations in which former users of tobacco products may need temporary relief from tobacco withdrawal symptoms due to environmental factors that may initiate a specific craving for nicotine. Such individuals may have completed a smoking cessation program, and/or may also be utilizing a sustained action nicotine or nicotine substitute drug formulation and encounter unexpected cravings or desires for nicotine products. Embodiments of the present invention feature the administration of lobeline in rapid acting dosage forms to alleviate acute nicotine craving.

Such a broad spectrum of applications is not found in other nicotine withdrawal remedies. The administration of lobeline in a non-invasive drug formulation which is effective is surprising and unexpected.

Administration to the sublingual mucosa avoids first pass metabolism and allows the lobeline to be received at nicotine receptor sites in the brain to alleviate nicotine withdrawal symptoms.

Other features and advantages of the present invention are disclosed in the following examples which exemplify preferred embodiments of the present invention.

EXAMPLE I

Sublingual Tablets

Sublingual tablets are made in accordance with the formulation set forth in Table I.

TABLE I

| | |
|---|---|
| Lobeline Sulfate | 2.5 mg |
| Mannitol, USP (DC grade) | 31.5 mg |
| Microcryst, Cellulose | 40.35 mg |
| Sodium Starch Glycolate NF | 2.6 mg |
| Sodium Saccharin, USP | 0.5 mg |
| Flavor S.D. Peppermint, FCC | 0.75 mg |
| Magnasweet Mm 188M | 0.5 mg |
| Vanilla flavor #800 | 0.2 mg |
| D&C Yellow #10, Aluminum Lake | 0.2 mg |
| Magnesium stearate, NF | 0.5 mg |
| Aerosil 200 | 0.4 mg |
| TOTAL | 80 mg |

The formulation set forth in Table I represents a preferred sublingual tablet formula. Individuals skilled in the art will recognize that modifications to the formulation can be readily made.

The preferred formulation features a tablet with 2.5 mg lobeline sulfate. This dosage can be varied to provide 0.6 mg or smaller and as much as 7.5 mg or more. However, lobeline amounts in less than 0.6 mg may require the administration of more than one tablet to obtain the desired effect. Higher doses could, however, be required for individuals highly addicted to nicotine. Lobeline, expressed as free base, amounts greater than 7.5 mg per dose are generally not required to produce the desired effect.

In the above formulation, mannitol, sodium saccharine, peppermint, magnasweet and vanilla are flavoring agents which are capable of masking the bitter taste of lobeline. The flavoring agents may be deleted without sacrificing efficacy. However, patient compliance may be more difficult. Flavorings may be altered to suit individual needs and tastes.

D&C yellow is used as a colorant. The colorant may be readily deleted or substituted with other dyes.

Magnesium stearate and Aerosil-200 are lubricants to release the tablet from press equipment. These ingredients may be substituted or deleted entirely depending on the manufacturing process.

Microcrystalline cellulose, mannitol and sodium starch glycolate provide the tablet core. The cellulose and starch facilitate binding the core ingredients and facilitate tablet disintegration in the presence of moisture. The relative amounts of these ingredients may be altered to adjust the disintegration rate of the tablet.

Quantities of all ingredients are weighed and all the ingredients, other than mannitol and Avicel, are passed through a 80 mesh stainless steel sieve. The materials are blended in a suitably sized polythene bag for about five minutes and transferred to suitable blender, such as a PK Blender. The required quantities of mannitol and Avicel are passed through a 40 mesh stainless steel sieve and added to the PK Blender with the other ingredients. The mixture is blended in the PK Blender for 10 minutes and unloaded. A sample of the blend is subjected to inspection for potency and other quality determining criteria. The bulk density is determined on the blend using bulk density apparatus set for 100 taps. The tablet press is set for the designated punches and the blend is compressed at 80 mg tablet weight.

Tablets are administered by placing a single tablet under the tongue. The tablet is allowed to disintegrate and release lobeline. The tablets described in this example disintegrate within seconds of being placed under the tongue. The lobeline is absorbed by the sublingual mucosa.

EXAMPLE II

This example features the use of 2.5 mg lobeline sulfate sublingual tablets.

Experience of JG

JG is a 54 year old male who has smoked 1 to 1½ packs of cigarettes per day for 40 years. He wants to quite smoking and has tried unsuccessfully to quit one time in the past.

J.G. was given 12 2.5 mg lobeline-SL tablets to evaluate as aids in smoking cessation. On the morning of day number one he self-administered two tablets sublingually. One hour later he self-administered one tablet and then took one more approximately three hours later. He smoked five cigarettes over the course of day number one.

One the second day JG took two tablets, one in the morning and one in the early afternoon. He smoked only two cigarettes that day.

On the third day JG took one-half of a tablet at three separates times, spread evenly throughout each day. He smoked only two cigarettes that day.

On the fourth day, JG took one-half of a tablet at two separate times, one in the morning and one in the afternoon. He smoked only two cigarettes on that day.

On the fifth day, JG took one-half of a tablet in the morning. He smoked only one cigarette that day.

JG continued taking one-half of a tablet daily until the supply was exhausted. During this time he smoked only one or two cigarettes each day.

When asked the reason he reduced his smoking level, he replied that he had much less desire to smoke and the cigarettes tasted bad when he did smoke.

Experience of SG

SG is a 44-year old male who has smoked 1 to 1½ packs of cigarettes per day for 15 years. He wants to quit smoking and has tried to quit ten times in the past, although unsuccessful in each case. He recently obtained a supply of nicotine transdermal patches to use in a smoking cessation program. However, he did not use them since he believes he would not be able to refrain from smoking and would, therefore, smoke cigarettes while using the patch and suffer the detrimental consequences of exposure to excess nicotine.

SG was given eight 2.5 mg lobeline-SL tablets to evaluate as an aid for smoking cessation. On the morning of day number one he self-administered two tablets sublingually. Two and one-half hours later he self-administered a third tablet and then a fourth tablet approximately three hours later. He smoked only two cigarettes on day one, compared to the 20 to 30 he would have normally smoked.

On the second day, SG took the remaining four tablets periodically throughout the day and smoked four cigarettes.

When asked why he smoked fewer than his usual number of cigarettes, he responded that he just did not have the urge to smoke. Three weeks after this two-day evaluation SG was smoking only 7 or 8 cigarettes per day.

Thus, while preferred embodiments of the present invention have been described, the present invention is capable of variation and modification and, therefore, the present invention should not be limited to the precise details set forth, but should include such changes and alterations as fall within the purview of the following claims.

What is claimed is:

1. A method of treating nicotine withdrawal symptoms, comprising:
   administering to a subject an effective amount of lobeline or lobeline analog to the sublingual mucosa, prior to or during a period in which the subject is experiencing nicotine withdrawal symptoms, said lobeline or lobeline analog absorbed through the sublingual mucosa to alleviate the subject's desire for nicotine; said lobeline or lobeline analog administered as a sublingual tablet, said sublingual tablet comprising lobeline or a lobeline analog in a tablet core having disintegrants capable of causing tablet disintergration within a five minute period in the presence of oral secretions.

2. The method of claim 1 wherein the equivalent of 0.6 to 7.5 mg lobeline free base is administered per dose.

3. The method of claim 2 wherein said lobeline is administered as a soluble salt.

4. The method of claim 3 wherein said salt is a sulfate or hydrochloride salt.

5. The method of claim 1 wherein said lobeline is administered as a sublingual tablet.

6. The method of claim 1 wherein said lobeline is available for absorption within a five-minute period.

7. The method of claim 1 wherein said lobeline is available for absorption within a two-minute period.

8. As an article of manufacture, a dosage form for treating nicotine withdrawal symptoms comprising:

a sublingual tablet comprising an effective amount of lobeline or lobeline analog held in a tablet core comprising disintegrants for application to the sublingual mucosa, said sublingual tablet releasing said lobeline or lobeline analog upon disintegration of the sublingual tablet within a five minute period and said lobeline or lobeline analog being absorbed through the mucosa to alleviate nicotine withdrawal symptoms.

9. The dosage form of claim 8 wherein said sublingual tablet disintegrates within a two-minute period.

10. The dosage form of claim 8 wherein said effective amount is the equivalent of 0.6 to 7.5 mg of lobeline free base per dose.

11. The dosage form of claim 8 wherein said lobeline is a soluble salt.

12. A method of treating nicotine withdrawal symptoms, comprising:

(a) administering to a subject an effective amount of nicotine or lobeline or lobeline analog by a sustained release dosage form prior to or during a period in which the subject is experiencing nicotine withdrawal symptoms, said nicotine or lobeline or lobeline analog released from said sustained release dosage form providing a base level of nicotine or lobeline or lobeline analog to alleviate the subject's long term desire for nicotine; and (b) administering to a subject an effective amount of lobeline or lobeline analog to the sublingual mucosa, prior to or during a period in which the subject is experiencing nicotine withdrawal symptoms, said lobeline or lobeline analog absorbed through the sublingual mucosa to alleviate the subject's acute desire for nicotine, said lobeline or lobeline analog administered as a sublingual tablet, said sublingual tablet comprising lobeline or lobeline analog in a tablet core having disintegrants capable of causing tablet disintegration within a five minute period in the presence or oral secretions.

* * * * *